United States Patent [19]

Barcellona et al.

[11] Patent Number: 4,498,496
[45] Date of Patent: Feb. 12, 1985

[54] MIXING OF GASEOUS SUBSTANCES

[75] Inventors: Alessandro Barcellona, Turin; Guido Ferrando Gorin, Cirié ; Aldo Lausarot, Torre Pellice, all of Italy

[73] Assignee: Fiat Auto S.p.A., Turin, Italy

[21] Appl. No.: 399,150

[22] Filed: Jul. 16, 1982

[30] Foreign Application Priority Data

Jul. 22, 1981 [IT] Italy ............................ 68016 A/81

[51] Int. Cl.³ .......................................... F16K 19/00
[52] U.S. Cl. ...................................... 137/599; 137/606
[58] Field of Search ........................ 137/599, 606, 607

[56] References Cited

U.S. PATENT DOCUMENTS

| | | | |
|---|---|---|---|
| 3,827,457 | 8/1974 | Vutz | 137/599 |
| 3,830,256 | 8/1974 | Cox | 137/599 |
| 3,886,971 | 6/1975 | Lundsgaard | 137/599 |
| 3,905,394 | 9/1975 | Jerde | 137/599 |
| 4,046,158 | 9/1977 | Hayashi | 137/599 X |
| 4,062,373 | 12/1977 | Clark | 137/607 X |
| 4,191,215 | 3/1980 | Gonner | 137/599 X |
| 4,420,009 | 12/1983 | Sharp | 137/599 X |

*Primary Examiner*—Robert G. Nilson
*Attorney, Agent, or Firm*—Sughrue, Mion, Zinn, Macpeak, and Seas

[57] ABSTRACT

The apparatus comprises a distributor device having two inlets connectible to two sources for supplying the gases to be mixed and a plurality of outlets each of which is connected to a first end of a respective capillary tube. The distributor device is arranged to connect each capillary tube to one or other of the two supply sources so that mixtures of the two gases are formed in a mixing chamber into which the other ends of the capillary tubes open, the mixtures containing the two gases in proportions which differ according to a number of capillary tubes traversed by each gas. The apparatus includes control means for causing the sequential formation of mixtures containing different proportions of the two gases and the supply of these mixtures to an outlet from the apparatus.

2 Claims, 6 Drawing Figures

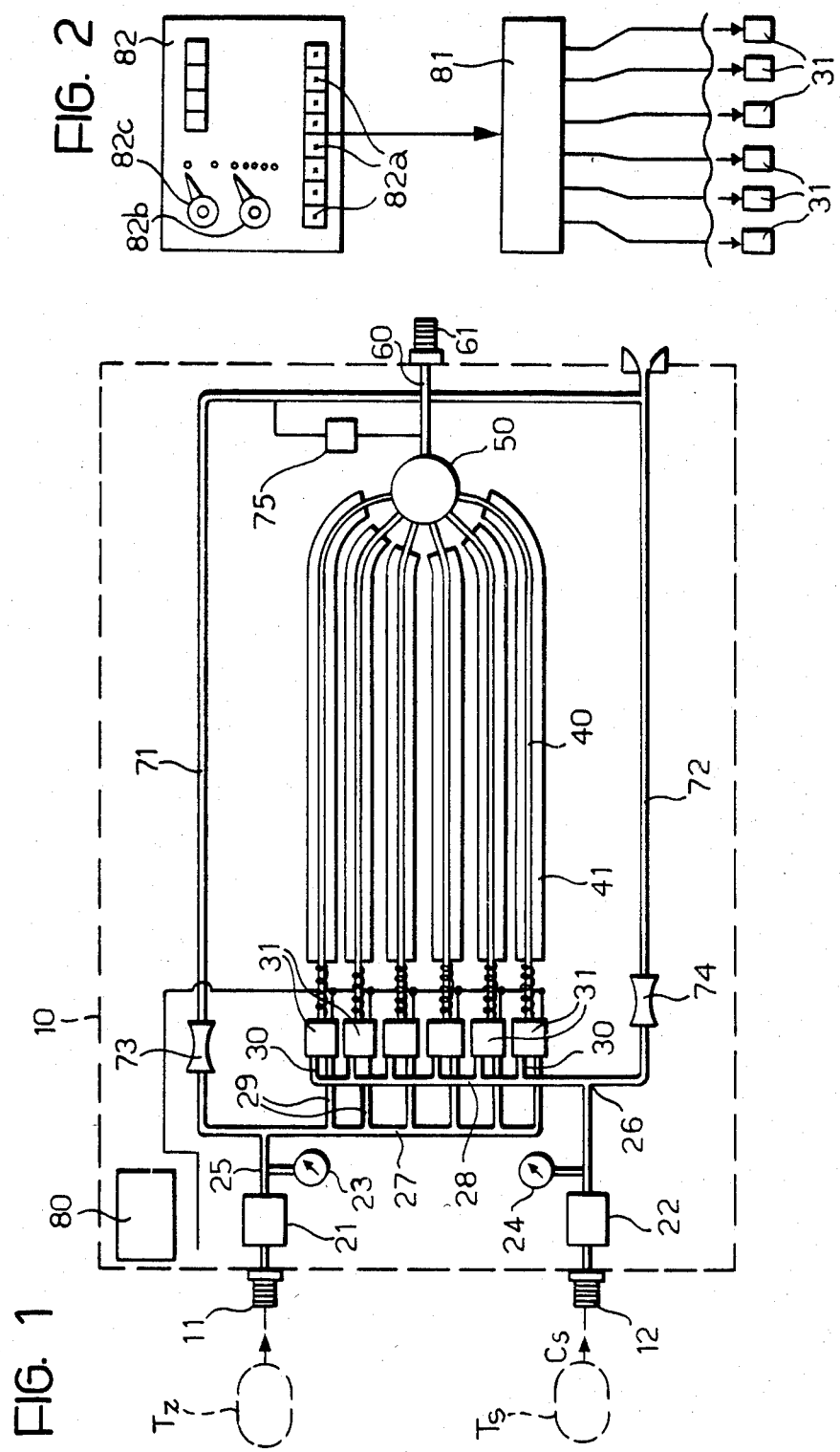

MIXING OF GASEOUS SUBSTANCES

BACKGROUND OF THE INVENTION

The present invention relates to apparatus for the controlled mixing of two gaseous substances and relates particularly to apparatus for the preparation of mixtures for calibrating analysers for exhaust gases from internal combustion engines.

In order to form a calibration curve for an analyser, it is necessary to feed samples of gaseous mixtures of known composition successively to its input. These samples are obtained by mixing a first gas, termed the zero gas, with a second gas, termed the span gas.

The zero point on the calibration curve can be defined by supplying the analyser with the zero gas while intermediate points and the full scale reading on the calibration scale can be defined by supplying the analyser with mixtures in which the zero gas and the span gas are present in known, increasing proportions.

SUMMARY OF THE INVENTION

The present invention provides apparatus for the controlled mixing of two gases supplied by two separate sources, comprising:

a plurality of identical capillary tubes a distributor device having two inlets each connectible to a respective one of the two supply sources and being arranged to connect each inlet to a different group composed of a selected number of the capillary tubes to supply the respective gas thereto;

a mixing chamber communicating with the capillary tubes to receive gas therefrom; and a duct for supplying a gaseous mixture formed in the mixing chamber, in use, to an outlet from the apparatus, the mixture containing the two gases in proportions which differ according to the number of capillary tubes traversed by each gas.

By virtue of this characteristic, the apparatus according to the invention allows mixtures to be obtained in which the two gases are present in known, controlled concentrations. In particular, in its application to the calibration of analysers, the apparatus according to the invention allows the calibrating operations to be carried out more quickly since it suffices to provide two sources containing respectively the zero gas and the span gas at a concentration corresponding to the full scale point on the calibration curve and other sources (for example cylinders) for supplying sample mixtures for defining intermediate points on the calibration curve of the analyser are no longer required.

The distributor device may include a plurality of valves connected one to each capillary, the valves being operable independently to put each capillary into communication with a respective one of the gas sources, in use, or to cut off this communication. In a preferred embodiment, however, the distributor device comprises:

first and second intake manifolds each communicating with a respective one of the two inlets through a respective inlet duct and each having a plurality of outlet ducts, a plurality of valves each of which is connected to a respective outlet duct of the first intake manifold, to a respective outlet duct of the second intake manifold and to a first end of a respective capillary tube, the valves being operable independently to put the respective capillary tubes selectively into communication with the first intake manifold or with the second intake manifold.

The physical principle which governs the operation of the preferred apparatus according to the invention will now be illustrated briefly.

Two gases which do not react together, for example a zero gas Z, in the pure state, and a span gas S at a concentration $C_s$ in the zero gas Z, when mixed according to flow rates $Q_z$ and $Q_s$ give rise to a dynamic concentration $$C_o: C_o = C_s \cdot \frac{Q_s}{Q_s + Q_z} \qquad (I)$$

The flow rate q through a capillary tube is expressed by a function of the type:

$$q = f(\Delta P, L, S, \mu) \qquad (II)$$

where:
$\Delta P$ = pressure drop between the ends of the tube
$L$ = length of the tube
$S$ = cross-section of the tube
$\mu$ — viscosity of the gas which passes through the tube = $\mu(T)$
$T$ = temperature of the gas.

For a particular capillary, $\Delta P$ being the same, the flow rates for different gases, for example for the zero gas Z and the span gas S, depend solely on the viscosity;

$$q_z \propto K \cdot \frac{1}{\mu_z} \qquad (III)$$

$$q_s \propto K \cdot \frac{1}{\mu_s} \qquad (IV)$$

where:
$q_z$ = flow rate of the gas Z in the capillary
$q_s$ = flow rate of the gas S in the capillary
$\mu_z$ = viscosity of the gas Z
$\mu_s$ = viscosity of the gas S
$K$ = constant of proportionality.

In the apparatus according to the invention, if there are n identical capillary tubes and the span gas passes through x of these capillary tubes, the mixture of gases which forms in the mixing chamber is characterised by a dynamic concentration $C_o$ which can be expressed according to equation (I) in the form:

$$C_o = C_s \cdot \frac{xq_s}{xq_s + (n-x)q_z} \qquad (V)$$

If equations (III) and (IV) are taken into account, equation (V) may be rewritten in the form:

$$C_o = C_s \cdot \frac{x}{x + (n-x)\frac{\mu_s}{\mu_z}} \qquad (VI)$$

The span gas S is diluted with the zero gas Z to the concentration $C_s$ and has a viscosity which can be expressed in the form:

$$\mu_s = (1 - C_s)\mu_z + C_s \mu_s' \qquad (VII)$$

where: $\mu_s'$ is the viscosity of the gas S in the pure state.

By substituting the equation (VII) in the equation (VI), and simplifying, one obtains:

$$C_o = C_s \cdot \frac{x}{x + (n-x) + C_s \left( \frac{\mu'_s - \mu_z}{\mu_z} \right)} \quad \text{(VIII)}$$

In the case in which:

$$C_s \cdot \frac{\mu'_s - \mu_z}{\mu_z} = A \ll 1 \quad \text{(IX)}$$

(IX) becomes:

$$C_o = C_s \cdot x/n \quad \text{(X)}$$

This final relationship illustrates how the concentration $C_o$ at the output of n capillaries is directly proportional to the number of capillaries x traversed by the span gas supplied by its respective source at concentration $C_s$ in the zero gas Z.

$C_o$ thus varies from the zero value, when x=0 (only zero gas flows in the capillaries), to the value $C_s$, for x=n (only the span gas flowing in the capillaries) through a series of predetermined intermediate values obtained for x=1, 2, 3, ... n−1.

The condition (IX) is fully satisfied under all the normal conditions of use of the apparatus according to the invention for calibrating analysers, in which conditions the coefficient A assumes values of between $10^{-4}$ and $10^{-2}$.

BRIEF DESCRIPTION OF THE DRAWINGS

The invention will now be described purely by way of non-limiting example with reference to the appended drawings, in which:

FIG. 1 is a schematic view illustrating the component parts of the apparatus according to the invention and their interconnections, FIG. 2 is a block schematic diagram illustrating the structure of one of the elements shown in FIG. 1, and FIGS. 3 to 6 illustrate diagrammatically several possible operating cycles of the apparatus according to the invention.

DESCRIPTION OF THE PREFERRED EMBODIMENT

Figure 3:
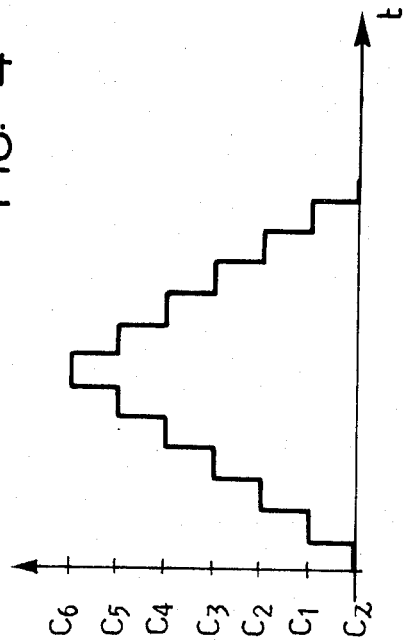

In FIG. 1, the casing of the apparatus according to the invention is generally indicated 10. To the apparatus are connected, through respective connectors 11, 12 carried by the casing, a first supply source $T_z$, containing a first gas, (for example a zero gas), and a second supply source $T_s$, containing a second gas, (for example a span gas diluted with a zero gas and at concentration $C_s$).

The inlet duct 25 of a first intake manifold 27 is connected to the connector 11 through a pressure regulator 21 with which a manometer 23 is associated.

The manifold 27 has a plurality of outlet ducts 29 each of which is connected to one of the inlets of a respective electromagnetically operated valve 31.

According to an entirely similar connection scheme, a second intake manifold 28 having an inlet duct 26 and a plurality of outlet ducts 30 is connected to the connector 12 through a pressure regulator 22 with which a manometer 24 is associated.

Each of the ducts 30 is connected to a further inlet of a respective valve 31.

The outlet of each of the valves 31 is connected to a first end of a capillary tube 40.

The other end of each capillary tube 40 opens into a mixing chamber 50.

The capillary tubes 40, which are identical to each other, are provided with thermally insulating means constituted, for example, by coatings of thermally insulating material 41 for maintaining all the capillary tubes 40 at the same temperature.

A duct 60 leaves the chamber 50 for carrying the supply of mixture formed in the mixing chamber 50.

The duct 60 is provided with an end connector 61 carried by the casing 10 which may be connected, for example, to the inlet of an analyser for exhaust gases from internal combustion engines.

Respective vent ducts 71, 72 are connected to the first intake manifold 27 and to the second intake manifold 28 for allowing the gaseous substances to be mixed to be discharged to the exterior, avoiding the mixing network formed by the capillary tubes 40 and the mixing chamber 50.

The vent ducts 71, 72 which have constrictions 73, 74 which allow a much smaller through-flow than the capillary tubes 40, have the function of maintaining the pressure regulators 21, 22 constantly in their dynamic operating range so as to prevent the gas flows through the two manifolds 27, 28 from varying during operation of the apparatus.

In the embodiment illustrated, a flow-meter regulator 75 is connected to the duct 60 which supplies the mixture formed in the mixing chamber 50 to the exterior to regulate the flow of gas from duct 60 through the vent duct 71 to thereby regulate the amount of gas mixture flowing to the analyzer through the end connector 61.

A control unit generally indicated 80 in FIG. 1 is connected to the apparatus and has the structure illustrated in greater detail by the block schematic diagram of FIG. 2.

In FIG. 2 a control circuit for the valves 31 is shown as 81 and an electrical operating circuit for the control circuit 81 is shown as 82.

The electrical circuit 82 is provided with a keyboard 82a and selectors 82b, 82c.

The operation of the apparatus will now be described with the aid of the charts of FIGS. 3 to 6, with non-limiting reference to the use of the invention for calibrating analysers for exhaust gases.

During operation in accordance with the chart of FIG. 3, the apparatus, after connection of the sources $T_z$ and $T_s$, is arranged to supply only the zero gas Z to the user (analyser).

This operating condition, which in the charts has been made to correspond with the origin of the abscissa, indicated by $C_z$, may be achieved by operating a first key of the keyboard 82a and, by means of the control circuit 81, positioning the valves 31 in the condition in which all the capillaries 40 are connected to the outlets 29 of the first manifold 27.

Subsequent operation of another key of the keyboard 82a, preferably adjacent that operated previously, displaces one of the valves 31 into the position in which its respective capillary tube 40 is connected to the second intake manifold 28. Thus the gas from the source $T_s$ (span gas) flows through one of the capillary tubes 40 while the gas from the source $T_z$ (zero gas) flows through the remaining capillary tubes 40, of which there are five in the embodiment illustrated.

A mixture is thus formed in the mixing chamber 50 in which the span gas S is present at a concentration $C_1$ which, according to equation (X) is equal to 1/6th of the concentration $C_s$ at which the span gas S is supplied by the source $T_s$.

Operation of a further key of the keyboard 82a preferably located the next along from those operated previously, can cause the displacement of two of the solenoid valves 31 into the positions in which their respective capillary tubes 40 are connected to the second intake manifold 28.

In this case, a mixture of gases is formed in the supply chamber 50 in which the span gas S is present at a concentration $C_2$ equal to 2/6th of the concentration $C_s$.

Subsequent operation of respective keys of the keyboard 82a can cause an increasing number of capillaries 40 to be connected to the second intake manifold 28 to form mixtures in the mixing chamber 50 in which the span gas S is present at increasing concentrations $C_3$, $C_4$, $C_5$, equal to 3/6th, 4/6th, 5/6th of the concentration $C_s$, until the situation is reached in which all the capillary tubes 40 are connected to the second intake manifold 28 and the mixture supplied to the exterior of the apparatus through the duct 60 contains the span gas S at the concentration $C_s$ at which it is supplied by the source $T_s$.

The mixtures supplied at concentrations $C_z$, $C_1 \ldots C_s$ during the operating cycle described, even if not in sequential order, may be used in forming the calibration curve of an analyser.

Figure 4:
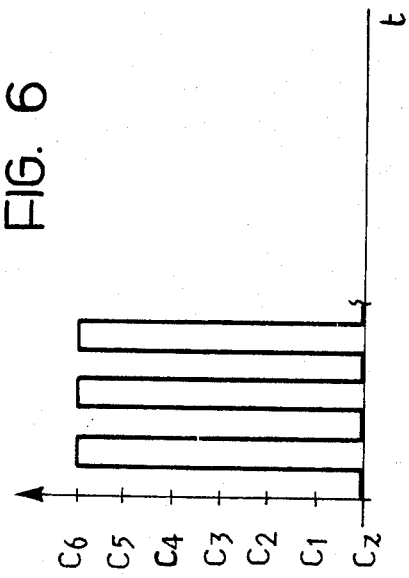
Figure 5:
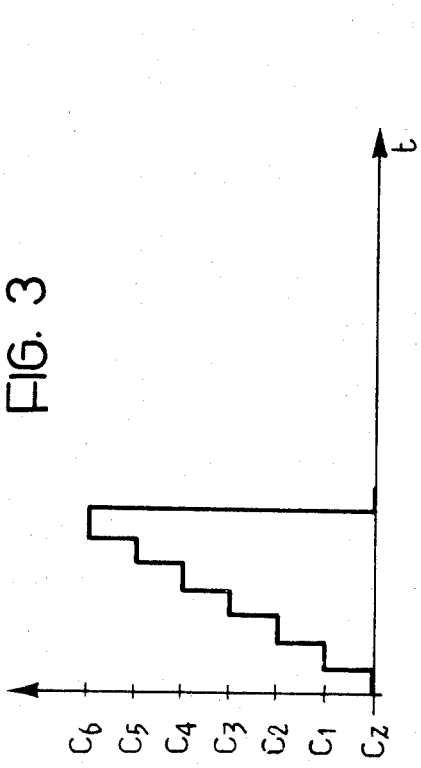
Figure 6:
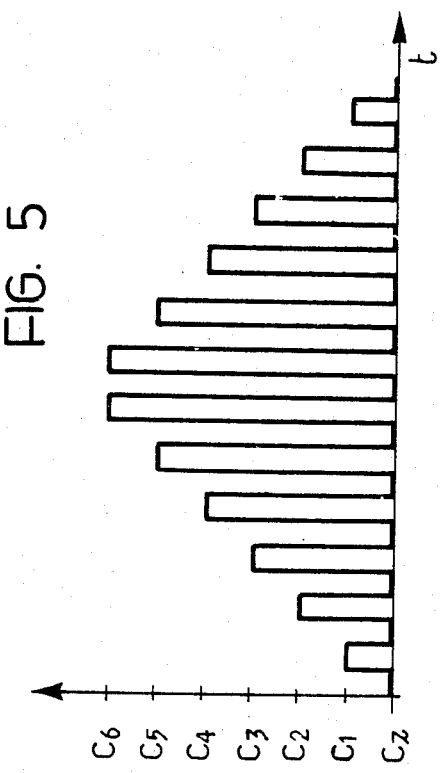

Different operating cycles may be achieved in accordance with the time charts illustrated in FIGS. 4 to 6.

In the chart of FIG. 4, after the sequential supply of mixtures containing increasing concentrations $C_2$, $C_1 \ldots C_s$ of the span gas S analogously to that formed in the cycle of FIG. 3, the apparatus successively supplies mixtures containing the span gas in decreasing concentrations.

According to the operating cycle of FIG. 5, which is substantially similar to the calibration cycle of FIG. 4, the supply of mixtures with increasing and decreasing concentrations of span gas is alternated periodically with a supply of the zero gas 2 alone at concentration $C_z$.

The cycle illustrated in FIG. 5 allows one to check that the positions of intermediate points on the calibration curve of the analyser are not influenced by the position of the zero point on this curve.

In the operating cycle of FIG. 6, the apparatus according to the invention supplies solely the zero gas coming from the source $T_z$ and solely the span gas S coming from the source $T_s$ alternately to check that the analyser does not present drift phenomena at the end points of the calibration curve.

The operating cycles illustrated in FIGS. 3 to 6 may be generated both manually, through the keyboard 82a, and automatically through an electrical processing circuit (for example a microprocessor) constituting one of the elements of the electrical operating circuit 82.

The selection of the automatic mode of operation instead of the manual mode of operation described above may be effected by operating the selector 82b which enables the operating cycle which the apparatus is to follow to be chosen, the selector 82c, which allows the time for which the two gases are to be supplied to the capillary tubes to be chosen and also, in the case of the operating cycle illustrated in FIG. 6, the number of alternations of the supply of the zero gas and the span gas.

The possibility of controlling the apparatus through a processor located at a distance is also foreseen.

The selection of remote-control operation may be effected by operating the selector 82b.

Naturally, the princple of the invention remaining the same, the details of construction and the embodiments may be varied widely with respect to that described and illustrated.

In particular the control unit 80 could be designed to allow operating cycles different from those described and illustrated in FIGS. 3 to 6 without thereby departing from the scope of the present invention.

What is claimed is:

1. Apparatus for the controlled mixing of two gasses supplied by two separate sources, comprising:
   a plurality of identical capillary tubes;
   a distributor device;
   two connectors each defining a respective inlet to said distributor device and each connectable to a respective one of said sources; said distributor device being arranged to connect each said inlet to a different group composed of a selected number of said capillary tubes for supplying a respective one of said gasses to each respective group;
   a mixing chamber communicating with said capillary tubes for receiving said gasses therefrom and forming a gaseous mixture of said gasses; and
   an outlet duct connected to said mixing chamber for receiving said gaseous mixture therefrom and supplying it to an outlet connector defining an outlet from the apparatus, said gaseous mixture containing said two gasses in proprotions which differ according to the number of capillaries in each said group,
   said distributor device comprising:
   a first intake manifold connected to a first connector of said two connectors;
   a first plurality of outlet ducts from said first intake manifold;
   a second intake manifold connected to the other connector of said two connectors;
   a second plurality of outlet ducts from said second intake manifold;
   a plurality of valves each of which is connected to a respective outlet duct of said first plurality of outlet ducts, to a respective outlet duct of said second plurality of outlet ducts, and to a first end of a respective capillary tube, each said valve being operable independently to put the respective capillary tube into communication with a selected one of said outlet ducts,
   each manifold being connected to a respective one of said connectors through a respective pressure regulator and a respective vent duct having constriction means therein being provided downstream of the pressure regulator for partially venting gas from the respective source from the apparatus.

2. Apparatus as claimed in claim 1 wherein a flow regulator is connected between said outlet duct and one of said vent ducts for regulating the gas flow from said outlet duct through one of said vent ducts to regulate the amount of gaseous mixture flowing through said outlet connector.

* * * * *